United States Patent [19]

Eberlein et al.

[11] Patent Number: 5,468,766

[45] Date of Patent: Nov. 21, 1995

[54] 1,5,6,7-TETRAHYDRO-4H-INDAZOL-4-ONES

[75] Inventors: Wolfgang Eberlein; Wolfhard Engel; Gerhard Mihm; Klaus Rudolf; Günther Engelhardt, all of Biberach, Germany

[73] Assignee: Dr. Karl Thomae GmbH, Biberach an der Riss, Germany

[21] Appl. No.: 128,506

[22] Filed: Sep. 29, 1993

[30] Foreign Application Priority Data

Sep. 29, 1992 [DE] Germany .............. 42 32 544.7

[51] Int. Cl.⁶ .................. A61K 31/415; C07D 231/56
[52] U.S. Cl. ....................... 514/403; 548/360.1
[58] Field of Search ................... 548/360.1; 514/403

[56] References Cited

U.S. PATENT DOCUMENTS

| 3,691,180 | 9/1972 | Blatter. |
| 4,734,430 | 3/1988 | Le Tourneau. |
| 5,108,485 | 4/1992 | Doehner ........................ 548/360.1 |

FOREIGN PATENT DOCUMENTS 0470489  2/1992  European Pat. Off. .

OTHER PUBLICATIONS

J. Het. Chem., 19; pp. 1355–1361 "Reaction of 2-Dimethylaminomethylene-1,3-diones with Dinucleophiles I. Synthesis of 1,5-Disubstituted 4-Acylpyrazoles", P. Schenone et al. (1983).

Primary Examiner—Robert W. Ramsuer
Attorney, Agent, or Firm—R. P. Raymond; M-E. M. Devlin; A. R. Stempel

[57] ABSTRACT

Pharmaceutical compositions are described which contain 1,5,6,7-tetrahydro-4H-indazol-4-ones of the formula

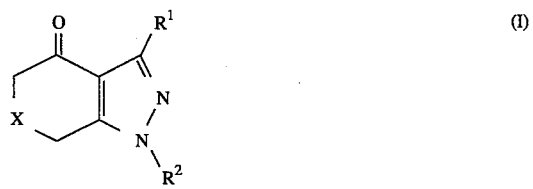

some of these substances themselves being new. The pharmaceutical compositions may be used as analgesics, antipyretics and antiphlogistics.

5 Claims, No Drawings

1,5,6,7-TETRAHYDRO-4H-INDAZOL-4-ONES

The invention relates to pharmaceutical compositions containing 1,5,6,7-tetrahydro-4H-indazol-4-ones, new 1,5,6,7-tetrahydro- 4H-indazol-4-ones, processes for preparing them and the use of these substances in pharmaceutical compositions as analgesics, antipyretics and antiphlogistics.

1,5,6,7-tetrahydro-4H-indazol-4-ones have been described as chemical compounds, e.g. in J. Het. Chem. 19: 1355 (1982); J. Org. Chem. 52:4384 (1987); J. Chem. Research 1401 (1986); J. Chem. Soc. 803 (1953).

Various pharmacological properties of 1,5,6,7-tetrahydro-4H-indazol- 4-ones, which are not covered by general formula I which follows, are known from the following publications, for example:

a.) compounds for an analgesic and anti-inflammatory activity are known from Il Farmaco, Ed. Sci. 42: 259 (1987); Il Farmaco, Ed. Sci. 43:763 (1988) and U.S. Pat. No. 3,657,438;

b.) compounds with a broncholytic and antibiotic activity are known from Heterocycles 32:41 (1991); U.S. Pat. No. 4,734,430 and U.S. Pat. No. 4,734,429;

c.) compounds with an antiviral activity are known from U.S. Pat. No. 3,691,180.

It has now been found that the 1,5,6,7-tetrahydro-4H-indazol- 4-ones of the formula

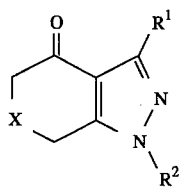

(I)

and the optically active antipodes thereof, provided that they contain an optically active carbon atom, have valuable pharmacological properties, in particular an analgesic, antipyretic and/or antiphlogistic activity.

In the above formula I $R^1$ and $R^2$, which may be identical or different, each represent a hydrogen atom, a straight-chained or branched $C_{1-6}$-alkyl group optionally substituted by a phenyl, fluorophenyl, chlorophenyl or bromophenyl group, or a phenyl group which may optionally be substituted by a halogen atom, and X represents a single bond, a methylene group which may optionally be substituted by one or two $C_{1-3}$ alkyl groups, or an ethylene group.

The 1,5,6,7-tetrahydro-4H-indazol-4-ones of formula I which are new are those wherein $R^1$ denotes a hydrogen atom and $R^2$ denotes a straight-chained or branched $C_{2-6}$-alkyl group or $R^1$ denotes a phenyl group and $R^2$ denotes a straight-chained or branched $C_{2-6}$-alkyl group or $R^1$ denotes a halophenyl group and $R^2$ denotes a straight-chained or branched $C_{1-6}$-alkyl group.

The present invention thus relates to the new pharmaceutical compositions containing a compound of formula I which are suitable for treating pain, fever and inflammation and for overcoming the symptoms of catarrhal diseases, the new 1,5,6,7-tetrahydro-4H-indazol-4-ones of formula I above and processes for preparing them.

Compounds of formula I which are preferred on account of their special activities are those wherein $R^1$ denotes a hydrogen atom or a methyl group, $R^2$ denotes a methyl, ethyl, propyl, isopropyl, benzyl or phenyl group and X denotes a methylene group or a methylene group substituted by 2 methyl groups.

A particularly preferred compound is the compound of formula I wherein $R^1$ denotes a hydrogen atom, $R^2$ denotes a methyl group and X denotes a methylene group. This compound has already been described as a starting compound for preparing compounds with an analgesic and antiinflammatory activity in Il Farmaco Ed. Sci. 42:259 (1987) and Il Farmaco Ed. Sci. 47:567 (1992) but the articles make no mention of any pharmacological properties of the starting compound itself. It is therefore highly surprising that this compound should prove to have very good analgesic, antipyretic and antiphlogistic properties, which have not been acknowledged hitherto.

In U.S. Pat. No. 3,657,438, the compound of formula I wherein $R^1$ represents a methyl group, $R^2$ a benzyl group and X a methylene group, is used as a starting compound for preparing compounds having an antiinflammatory activity; there is no mention of any pharmacological properties adhering to the starting compound itself. It has now been found, surprisingly, that this compound also has the valuable properties mentioned above.

The preparation of compounds of formula I wherein $R^1$ represents a hydrogen atom, $R^2$ a methyl or phenyl group and X a methylene or dimethylmethylene group, is described in J. Het. Chem. 19: 1355 (1982).

The preparation of the compound of formula I wherein $R^1$ denotes a hydrogen atom, $R^2$ a benzyl group and X a methylene group, is known from Heterocycles 32:41 (1991). The preparation of the compound of formula I wherein $R^1$ denotes a methyl group, $R^2$ a phenyl group and X a methylene group, is apparent from J. Chem. Soc. 803 (1953).

The above-mentioned new 1,5,6,7-tetrahydro-4H-indazol-4-ones are obtained, according to the invention, by the following methods:

a.) Preparation of compounds of formula I wherein $R^1$ has the meanings given hereinbefore, with the exception of a hydrogen atom, by reacting a compound of formula II

(II)

wherein X is as hereinbefore defined and $R^1$ has the above meanings with the exception of a hydrogen atom, with a hydrazine of formula III $H_2N - NH - R^2$     (III)

wherein $R^2$ is again as hereinbefore defined.

The reaction is preferably carried out in a solvent such as methanol, ethanol, isopropanol, tetrahydrofuran, dioxane, methylene chloride or benzene, at temperatures between 0° C. and the reflux temperature of the reaction mixture. The isolation of the end products is carried out in known manner by removing the solvent.

b.) Preparation of compounds of formula I wherein $R^1$ represents a hydrogen atom, by reacting a compound of formula IV

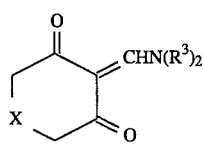

(IV)

wherein X is as hereinbefore defined and $R^3$ denotes an alkyl group, preferably methyl, with a hydrazine of the above formula III.

The hydrazine of formula III and the compound of formula IV are dissolved in methanol, ethanol, isopropanol, tetrahydrofuran, dioxane or methylene chloride and the solutions are combined at temperatures around 0° C. After the mixture has been stirred for several hours at temperatures between 0° C. and the reflux temperature of the reaction mixture, the solvent is eliminated, e.g. by distillation.

The starting substances according to formula II can be prepared using the procedures described in J. Chem. Soc. 803 (1953) and Synthesis 925 (1978). For the preparation of the starting substances of formula IV, reference is made to J. Het. Chem. 19: 1355 (1982).

As already mentioned hereinbefore, the compounds of general formula I have valuable pharmacological properties, particularly antipyretic, analgesic and antiphlogistic properties.

In particular, the compound 1-methyl-1,5,6,7-tetrahydro-4H-indazol-4-one (substance A) was tested as follows:

1. The effect against the pain of inflammation in the rat was tested using the method of RANDALL and SELITTO (Arch. int. Pharmacodyn. 111:409 (1957)). The test substances were administered to male rats weighing between 100 and 130 g as a trituration in 1% methylcellulose (1.0 ml/100 g of animal) by oesophageal tube 90 minutes after the subcutaneous administration of the yeast. The pain threshold measured 45, 90 and 180 minutes after the administration of various doses was used to determine, by linear regression analysis, an $ED_{50}$, being the dosage which brought about a 50% rise in the pain threshold.

The following Table shows the values found:

| Substance | $ED_{50}$ mg/kg | |
|---|---|---|
| | after 45 min. | after 90 min. |
| A | 3.1 | 2.1 |

2. The activity against the pain caused by heat in mice was tested using the method of CHEN and BECKMAN (Science 113:631 (1951)). Male mice with an average weight of 20 g were given the test substances as a trituration in 1% methylcellulose (0.1 ml/10 g of animal) by oesophageal tube. The increase in the individual reaction time observed after various doses was used to calculate an ED100 by linear regression analysis, being the dosage which resulted in a doubling of the reaction time.

The Table which follows contains the results found:

| Substance | $ED_{100}$ mg/kg |
|---|---|
| A | 159 |

3. The activity against mechanically induced pain was tested using the tail clip method according to HAFFNER (Dtsch. med. Wschr. 54:731 (1929)). Male mice weighing between 19 and 24 g were given the test substances as a trituration in 1% methylcellulose (0.1 ml/10 g of animal) by oesophageal tube. At 30 minute intervals after treatment it was noted how many mice were no longer reacting to the presence of the clip.

An $ED_{50}$ was calculated by probit analysis from the percentage of animals which showed no reaction to pain after the various doses.

The following Table contains the results found:

| Substance | $ED_{50}$ mg/kg |
|---|---|
| A | 45.2 |

4. The effect on body temperature was tested on normothermic rats weighing between 120 and 140 g. The test substances were administered by oesophageal tube as a trituration in 1% methylcellulose (1.0 ml/100 g of animal). From the lowering of rectal temperature observed after the various doses, an $ED_{-1.5° C.}$ was calculated by linear regression analysis as being the dosage which brought about a lowering of body temperature by 1.5° C.

The following Table contains the results found:

| Substance | $ED_{-1.5° C.}$ mg/kg |
|---|---|
| A | 7.1 |

5. The acute toxicity was determined on mice or rats of both sexes with an average weight of 20 g. The test substance was administered by oesophageal tube as a trituration in 1% methylcellulose (0.2 ml/10 g of animal). The $LD_{50}$ was calculated (where possible) according to LITCHFIELD and WILCOXON (J. Pharmacol. exp. Therap. 96:99 (1949)) from the percentage of animals which died within 14 days after receiving various doses.

The following Table contains the results found:

| Substance | $LD_{50}$ mg/kg | |
|---|---|---|
| | mouse | rat |
| A | 1670 | 1090 |

In view of their pharmacological properties the compounds of general formula I are analgesics/antipyretics of the aminophenazone type. They are therefore suitable for treating painful conditions such as headache, toothache, menstrual pain, neuralgia, migraine, post-operative and post-traumatic pain and also for controlling fever and inflammations and the symptoms of catarrhal diseases.

For this purpose the compounds of general formula I, optionally in conjunction with other active substances, may be formulated with one or more inert carriers and/or diluents, e.g. water, maize starch, potato starch, lactose, glucose, microcrystalline cellulose, magnesium stearate, polyvinylpyrrolidone, hard fat, carboxymethylcellulose or suitable mixtures thereof, to produce conventional galenic preparations such as plain or coated tablets, capsules, powders, suppositories, suspensions and solutions. The individual dosage for adults is 25 to 1200 mg, appropriately 50 to 600 mg, but preferably 100 to 300 mg.

The Examples which follow are intended to illustrate the invention:

EXAMPLE 1

1-Methyl-1,5,6,7-tetrahydro-4H-indazol-4-one

A solution of 46.1 g (1.0 mol) of methylhydrazine in 400 ml of methanol is slowly added dropwise at ambient temperature to a solution of 167.2 g (1.0 mol) of 2-(dimethylaminomethylene)-cyclohexane- 1,3-dione in 2000 ml of methanol. The reaction mixture is then refluxed for 1.5 hours. It is evaporated dryness in vacuo and the crude product obtained is purified by chromatography on silica gel (made by Baker, 30–60 μm) with a mixture of ethyl acetate and cyclohexane= 9:1.

By recrystallising from diisopropylether, the desired compound is obtained in a yield of 89.3% of theory. Colourless crystals, m.p. 96°–97° C.

EXAMPLE 2

1-Ethyl-1,5,6,7-tetrahydro-4H-indazol-4-one

Prepared analogously to Example 1 starting from ethylhydrazine and 2-(dimethylaminomethylene)-cyclohexane-1,3-dione.

Melting point: 60°–61° C.
Yield: 88% of theory

EXAMPLE 3

1-Propyl-1,5,6,7-tetrahydro-4H-indazol-4-one

Prepared analogously to Example 1 starting from propylhydrazine and 2-(dimethylaminomethylene)-cyclohexane-1,3-dione.

Melting point: 47°–48° C.
Yield: 70% of theory

EXAMPLE 4

1-(1-Methylethyl)-1,5,6,7-tetrahydro-4H-indazol-4-one

Prepared analogously to Example 1 starting from isopropylhydrazine and 2-(dimethylaminomethylene)-cyclohexane- 1,3-dione.

Melting point: 84°–85° C.
Yield: 58% of theory

EXAMPLE 5

1-Benzyl-1,5,6,7-tetrahydro-4H-indazol-4-one

Prepared analogously to Example 1 starting from benzylhydrazine and 2-(dimethylaminomethylene)-cyclohexane-1,3-dione.

Melting point: 60° C.
Yield: 72% of theory

EXAMPLE 6

1-Phenyl-1,5,6,7-tetrahydro-4H-indazol-4-one

Prepared analogously to Example 1 starting from phenylhydrazine and 2-(dimethylaminomethylene)-cyclohexane-1,3-dione.

Melting point: 140° C.
Yield: 49% of theory

EXAMPLE 7

1,6,6-Trimethyl-1,5,6,7-tetrahydro-4H-indazol-4-one

Prepared analogously to Example 1 starting from methylhydrazine and 2-(dimethylaminomethylene)-5,5-dimethyl-cyclohexane- 1,3-dione.

Melting point: 74°–75° C.
Yield: 32% of theory

EXAMPLE 8

1-Ethyl-3-methyl-1,5,6,7-tetrahydro-4H-indazol-4-one

Prepared analogously to Example 1 starting from 2-acetyl-cyclohexane- 1,3-dione and ethylhydrazine.

Melting point: 66°–67° C.
Yield: 43% of theory

PHARMACEUTICAL EXAMPLES

EXAMPLE I

Tablets Containing 125 Mg of
1-Methyl-1,5,6,7-tetrahydro- 4H-indazol-4-one

| Composition: | |
| --- | --- |
| Active substance | 125.0 mg |
| Microcrystalline cellulose | 63.5 mg |
| Lactose, ready for tablet making | 110.0 mg |
| Magnesium stearate | 1.5 mg |
| | 300.0 mg |

Preparation:

The excipients are thoroughly mixed with the active substance and compressed into tablets. Round biplanar tablets are obtained, facetted on both sides and notched on one side.

Weight of tablet: approx. 300 mg
Diameter of tablet: 10 mm

EXAMPLE II

Coated Tablets Containing 125 Mg of
1-Methyl-1,5,6,7-tetrahydro- 4H-indazol-4-one

| Composition: | |
| --- | --- |
| Active substance | 125.0 mg |
| Microcrystalline cellulose | 63.5 mg |
| Lactose, ready for tablet making | 110.0 mg |
| Magnesium stearate | 1.5 mg |
| | 300.0 mg |

Preparation:

The excipients are thoroughly mixed with the active substance and compressed into tablets. The tablets obtained are coated with conventional sugar coating suspension and then with pure sugar syrup in a coating pan to give a finished weight of 390 mg per coated tablet.

Weight of core: about 300 mg
Diameter of core: 10 mm
Appearance: round, biconvex

EXAMPLE III

Granules Containing
1-Methyl-1,5,6,7-tetrahydro-4H-indazol- 4-one

| Composition: | |
|---|---|
| (01) Active substance | 12.5% |
| (02) Sorbitol | 86.0% |
| (03) Silicon dioxide | 1.3% |
| (04) Magnesium stearate | 0.2% |
| | 100.0% |

Preparation:

Components (01), (02) and (03) are mixed together and moist-granulated with ethanol. After drying and screening (mesh size 1.0 mm) the granules are mixed with (04) and packed into sachets. A sachet containing 1 g of granules contains 125 mg of active substance.

EXAMPLE IV

Fine Granules Containing
1-Methyl-1,5,6,7-tetrahydro-4H-indazol- 4-one

| Composition: | |
|---|---|
| (01) Active substance | 12.5% |
| (02) Polyvinylpyrrolidone | 2.8% |
| (03) Lactose | 83.0% |
| (04) Silicon dioxide | 1.2% |
| (05) Magnesium stearate | 0.5% |
| | 100.0% |

Preparation:

Ingredient (03) with a particle size of 0.2–0.45 mm is placed in a rotating coating pan. Ingredient (02) is dissolved in isopropanol and then (01) and (04) are suspended therein. The suspension is carefully sprayed on to the lactose crystals in the coating pan, with a supply of dry air. After drying, ingredient (05) is added and a quantity of granules containing 125 mg of active substance is packed into sachets.

EXAMPLE V

Injectable Solution Containing 125 Mg of
1-Methyl- 1,5,6,7-tetrahydro-4H-indazol-4-one

| Composition: | |
|---|---|
| Active substance | 125.0 mg |

-continued

| Composition: | |
|---|---|
| Water for injections ad | 2 ml |

Preparation:

The active substance is dissolved at ambient temperature into water for injections. The solution is sterile-filtered, transferred into clean ampoules and autoclaved to 20 minutes at 121° C.

EXAMPLE VI

Suppositories Containing 200 Mg of
1-Methyl-1,5,6,7-tetrahydro- 4H-indazol-4-one

| Composition: | |
|---|---|
| Active substance | 200.0 mg |
| Solid fat (e.g. Witepsol H 19 and Witepsol W 45) | 1,500.0 mg |

Preparation:

The hard fat is melted. At 38° C. the ground active substance is homogeneously dispersed in the melt. This is then cooled to 35° C. and poured into slightly chilled suppository moulds.

EXAMPLE VII

Syrup Containing 125 Mg of
1-Methyl-1,5,6,7-tetrahydro- 4H-indazol-4-one

| Composition: | |
|---|---|
| Active substance | 2.50 g |
| Carboxymethylcellulose | 0.10 g |
| Methyl p-hydroxybenzoate | 0.05 g |
| Propyl p-hydroxybenzoate | 0.03 g |
| Saccharose | 10.00 g |
| Glycerol | 5.00 g |
| 70% sorbitol solution | 20.00 g |
| Flavouring | 0.30 g |
| Distilled water ad | 100.00 ml |

Preparation:

Distilled water is heated to 70° C. Methyl p-hydroxybenzoate and propyl p-hydroxybenzoate as well as glycerol and carboxymethylcellulose are dissolved therein with stirring. The mixture is cooled to ambient temperature and the active substance is added and dissolved therein with stirring. After the saccharose, sorbitol solution and flavouring have been added and dissolved the syrup is evacuated with stirring in order to eliminate air.

What is claimed is:

1. 1,5,6, 7-tetrahydro-4H-indazol-4-ones of the formula

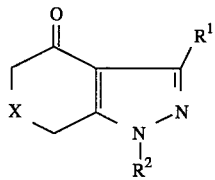

wherein $R^1$ is a hydrogen atom and $R^2$ is a straight-chained or branched $C_{2-6}$-alkyl group and X is a methylene group which may be substituted by one or two methyl groups.

2. The compound as recited in claim 1, 1-ethyl-1,5,6,7-tetrahydro-4H-indazol- 4-one.

3. The compound as recited in claim 1, 1-propyl-1,5,6,7-tetrahydro-4H-indazol- 4-one.

4. The compound as recited in claim 1, 1-(1-methylethyl)-1,5,6,7-tetrahydro- 4H-indazol-4-one.

5. A pharmaceutical composition of mater comprising a compound as recited in 1 together with a pharmaceutically acceptable carrier or diluent.

* * * * *